US012589193B2

(12) United States Patent     (10) Patent No.:    US 12,589,193 B2

Nishi et al.               (45) Date of Patent:     Mar. 31, 2026

---

(54) LIQUID SAMPLE PROCESSING DEVICE

(71) Applicant: PROVIGATE INC., Tokyo (JP)

(72) Inventors: Mitsumi Nishi, Tokyo (JP); Noriko Miyauchi, Tokyo (JP)

(73) Assignee: PROVIGATE INC., Tokyo (JP)

( * ) Notice: Subject to any disclaimer, the term of this patent is extended or adjusted under 35 U.S.C. 154(b) by 424 days.

(21) Appl. No.: 18/246,162

(22) PCT Filed: Oct. 25, 2021

(86) PCT No.: PCT/IB2021/059815
§ 371 (c)(1),
(2) Date: Mar. 21, 2023

(87) PCT Pub. No.: WO2022/064475
PCT Pub. Date: Mar. 31, 2022

(65) Prior Publication Data

US 2023/0364314 A1     Nov. 16, 2023

(30) Foreign Application Priority Data

Sep. 23, 2020    (JP) ................................. 2020-159187

(51) Int. Cl.
*A61M 1/34*        (2006.01)
(52) U.S. Cl.
CPC ....... *A61M 1/3431* (2014.02); *A61M 2205/75* (2013.01)
(58) Field of Classification Search
CPC ............... G01N 35/0099; G01N 35/10; G01N 35/1079; G01N 1/38; G01N 2001/381;
(Continued)

(56) References Cited

U.S. PATENT DOCUMENTS 4,046,145 A * 9/1977 Choksi .................. A61J 1/2096
                                  141/2
4,487,696 A * 12/1984 Ferrara .................. B01D 33/01
                                210/399
(Continued)

FOREIGN PATENT DOCUMENTS

CN       102252870 A    11/2011
JP       2007532260 A   11/2007
(Continued)

OTHER PUBLICATIONS

PCT International Search Report for PCT/IB2021/059815, mailed Dec. 21, 2021.

*Primary Examiner* — Tran M. Tran
(74) *Attorney, Agent, or Firm* — McBee Moore & Vanik IP, LLC

(57) ABSTRACT

A device that collects liquid includes a flow passage member (110) including a flow passage (111) that receives liquid at one end (113) of the flow passage (111) and that is capable of containing the received liquid (102); a tank (120) having an internal space (121) in which a processing solution (131) is contained, the tank (120) being configured to receive at least one end (113) of the flow passage member (110) and allow mixing of the processing solution (131) contained in the tank (120) and the liquid (102) contained in the flow passage (111) to start in the internal space (121); a pump (150) for discharging the mixed solution from the tank (120); and a filter (160) that separates one or more components of the mixed solution.

19 Claims, 14 Drawing Sheets

(58) Field of Classification Search
CPC .......... G01N 2001/382; G01N 2001/386–388;
G01N 2030/185; G01N 2035/1053; B01L
3/50215; A61M 1/3431
See application file for complete search history.

(56) References Cited

U.S. PATENT DOCUMENTS

| | | | | |
|---|---|---|---|---|
| 4,510,058 A * | 4/1985 | Cais | ......................... | G01N 30/58 |
| | | | | 210/657 |
| 4,892,710 A * | 1/1990 | Wong | ..................... | G01N 1/405 |
| | | | | 604/326 |
| 4,935,010 A * | 6/1990 | Cox | ..................... | A61M 39/045 |
| | | | | 604/167.03 |
| 5,062,310 A * | 11/1991 | Eaton | ..................... | G01N 30/18 |
| | | | | 73/866.5 |
| 5,186,839 A * | 2/1993 | Kimura | .............. | G01N 30/6021 |
| | | | | 210/656 |
| 5,266,193 A * | 11/1993 | Kimura | .............. | G01N 30/6021 |
| | | | | 210/656 |
| 5,277,873 A * | 1/1994 | Hsei | ......................... | B01L 3/502 |
| | | | | 494/20 |
| 5,364,533 A * | 11/1994 | Ogura | ..................... | A61B 5/154 |
| | | | | 210/504 |
| 5,378,360 A * | 1/1995 | Huse | ...................... | B01D 15/34 |
| | | | | 210/656 |
| 5,439,593 A * | 8/1995 | Price | ...................... | B01D 15/22 |
| | | | | 210/660 |
| 5,637,087 A * | 6/1997 | O'Neil | .................. | A61M 5/284 |
| | | | | 604/82 |
| 5,730,943 A * | 3/1998 | Ford | .................. | G01N 30/6039 |
| | | | | 73/61.52 |
| 5,888,826 A * | 3/1999 | Ostgaard | ................. | B01L 3/502 |
| | | | | 422/504 |
| 5,919,356 A * | 7/1999 | Hood | ....................... | G01N 1/14 |
| | | | | 210/85 |
| 5,996,811 A * | 12/1999 | Kitajima | ............... | B01D 61/18 |
| | | | | 210/488 |
| 6,177,008 B1 * | 1/2001 | Treiber | .................. | B01D 15/22 |
| | | | | 210/656 |
| 6,220,453 B1 * | 4/2001 | Kitajima | ........... | B01D 19/0031 |
| | | | | 210/473 |
| 7,025,212 B2 * | 4/2006 | Amano | .............. | B01D 39/2017 |
| | | | | 210/488 |
| 7,378,054 B2 | 5/2008 | Karmali | | |
| 8,133,456 B2 * | 3/2012 | Higashino | ........... | F16K 99/0001 |
| | | | | 422/503 |
| 9,176,035 B2 * | 11/2015 | Hur | ......................... | G01N 1/34 |
| 9,427,707 B2 * | 8/2016 | Montagu | ............... | G01N 33/48 |
| 9,574,978 B2 * | 2/2017 | Hur | ......................... | G01N 1/38 |
| 9,694,358 B2 * | 7/2017 | Luotola | ........... | A61B 5/150351 |
| 10,159,973 B2 * | 12/2018 | Kumakura | .............. | B01L 3/502 |
| 10,330,694 B2 * | 6/2019 | Stankus | ............ | G01N 35/1011 |
| 10,435,314 B2 * | 10/2019 | Murata | .................. | B01J 19/088 |
| 11,360,076 B2 * | 6/2022 | Johnson | ........... | A61B 5/150755 |
| 11,709,175 B2 * | 7/2023 | Hopper | .................. | B01L 3/502 |
| | | | | 435/6.12 |
| 12,332,234 B2 * | 6/2025 | Paulicka | ............... | B01L 3/5023 |
| 12,345,700 B2 * | 7/2025 | Sinn Blandy | ......... | B01L 3/5082 |
| 2003/0175167 A1 * | 9/2003 | Takanori | ............... | B01L 3/5021 |
| | | | | 422/534 |
| 2003/0206828 A1 | 11/2003 | Bell | | |
| 2005/0014273 A1 * | 1/2005 | Dahm | .................. | B01L 3/5635 |
| | | | | 436/45 |
| 2005/0101979 A1 | 5/2005 | Alden et al. | | |
| 2005/0196872 A1 | 9/2005 | Nguyen et al. | | |
| 2005/0232813 A1 * | 10/2005 | Karmali | .......... | A61B 5/150022 |
| | | | | 422/410 |
| 2006/0199275 A1 * | 9/2006 | Togawa | ............. | B01L 3/50825 |
| | | | | 210/450 |
| 2008/0300397 A1 * | 12/2008 | Kenrick | ............ | C12N 15/1017 |
| | | | | 210/203 |
| 2010/0093551 A1 | 4/2010 | Montagu et al. | | |
| 2012/0024788 A1 | 2/2012 | Kelso et al. | | |
| 2015/0153323 A1 * | 6/2015 | Huemer | ........... | B01L 3/502723 |
| | | | | 422/534 |

FOREIGN PATENT DOCUMENTS

| | | |
|---|---|---|
| JP | 2008157783 A | 7/2008 |
| JP | 2018529983 A | 10/2018 |
| JP | 2019074344 A | 5/2019 |
| JP | 2019537723 A | 12/2019 |
| WO | 2014023761 A1 | 2/2014 |
| WO | 2016073415 A2 | 5/2016 |
| WO | 2016073415 A3 | 8/2016 |
| WO | 2016156729 A1 | 10/2016 |
| WO | 2019025914 A1 | 2/2019 |

* cited by examiner

240

210

220

211

221

222

232

LIQUID SAMPLE PROCESSING DEVICE

CROSS-REFERENCE TO RELATED APPLICATIONS

This application is the National Stage entry of International Application No. PCT/JB2021/058915, filed 25 Oct. 2021, which claims priority to Japan No. 2020-159187, filed 23 Sep. 2020.

TECHNICAL FIELD

The present disclosure relates to devices for processing liquid samples, for example, a device for mixing a liquid sample with processing liquid to obtain processed liquid.

DESCRIPTION OF RELATED ART

It is desirable to reduce the size of devices included in systems for collecting a small amount of body fluid, such as blood, or other liquids and performing preprocessing for a test on the collected liquid. Smaller devices are also useful in point-of-care testing, and are also desired for use in tests performed on a small amount of specimen. The devices that are limited in size are desirably capable of, for example, efficiently preprocessing a small amount of specimen or removing or separating impurities undesirable for a measurement.

SUMMARY OF INVENTION

Here, it is recognized, for example, without limitation, that it is desirable to efficiently collect and preprocess liquid and efficiently extract the preprocessed liquid.

Some embodiments of the present disclosure provide a liquid collector (liquid collection apparatus or device). In some embodiments, the liquid collection device collects liquid. In some embodiments, the liquid collection device includes a flow passage member. The flow passage member may include a flow passage. In some embodiments, the liquid collection device includes the flow passage. In some embodiments, the flow passage is configured to receive the liquid at one end thereof. In some embodiments, the flow passage is capable of containing the received liquid. In some embodiments, the liquid collection device includes a tank. In some embodiments, the tank contains a processing solution. In some embodiments, the tank is configured to receive the flow passage member at a portion or an end thereof. In some embodiments, the tank is configured such that the processing solution contained in the tank and the liquid contained in the flow passage are mixed in an internal space thereof. The mixing may at least start in the internal space. In some embodiments, the liquid collection device includes a pump for discharging mixed liquid (hereinafter also referred to as a mixed solution) from the tank. In some embodiments, the liquid collection device includes a filter. The filter may be configured to separate one or more components of the mixed solution.

According to the above-described embodiments, for example, processes of collecting a relatively small amount of liquid and preprocessing the collected liquid can be efficiently performed.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

DETAILED DESCRIPTION OF A PREFERRED EMBODIMENT

Figure 1A:
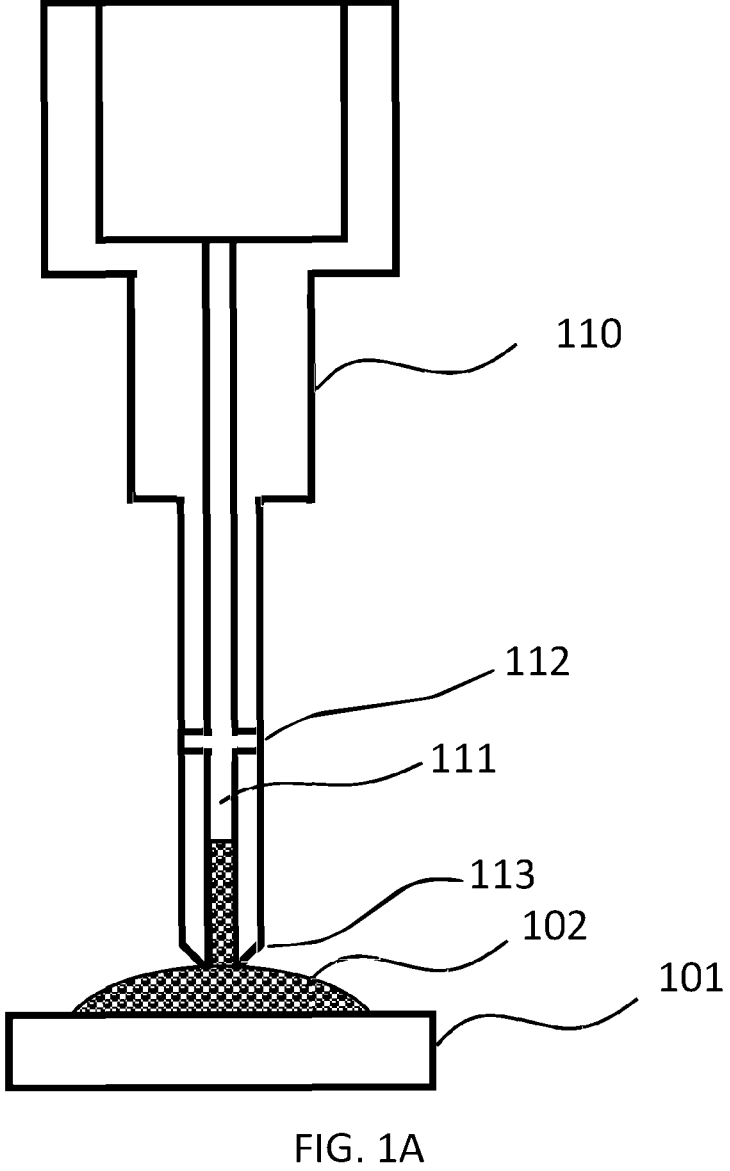
FIG. 1A is a sectional view illustrating a process of using a liquid collection device according to an embodiment.

In some embodiments, the liquid may be body fluid produced by secretion in a target subject, or liquid other than body fluid. The liquid other than body fluid may be liquid adhering to a target object or liquid not adhering to a target object. The liquid not adhering to a target object may be liquid contained in a target object.

The liquid to be collected may be a solution. The liquid may be body fluid, a solution derived from body fluid, or diluted body fluid. The liquid may be a solution other than (not derived from) body fluid, or a mixture of body fluid or a solution derived from body fluid with a solution not derived from body fluid. The solution may be a solution used for sample measurement or a solution used for calibration measurement. For example, the solution may be a reference solution or a calibration solution. The sample to be measured may be a specimen.

Examples of the body fluid include lymph fluid, tissue fluid such as inter-tissue fluid, intercellular fluid, and interstitial fluid, coelomic fluid, serous cavity fluid, pleural fluid, ascites fluid, pericardial fluid, cerebrospinal fluid, synovial fluid, and aqueous humor. Examples of the body fluid further include digestive juice, such as saliva, gastric juice, bile, pancreatic juice, and intestinal juice, sweat, tear, nasal mucus, urine, semen, vaginal fluid, amniotic fluid, and milk. The body fluid may be body fluid of an animal or body fluid of a human. The "body fluid" may be a solution. The solution may include a physiological buffer, such as phosphate-buffered saline (PBS) or N-tris (hydroxymethyl) methyl-2-aminoethanesulfonic acid (TES) buffer, containing a measurement target substance. The solution is not particularly limited as long as the measurement target substance is contained.

In some embodiments, the body fluid may be blood. In some embodiments, the blood may be collected. For example, the blood may be collected at the same time as the time when bleeding is caused by a puncture. For example, the blood may be sucked through an inserted needle. In some embodiments, a puncturing tool (for example, a needle or an injection needle; the same applies hereinafter) may be disposed at a distal end of a capillary tube. In some embodiments, the capillary tube may be formed as a puncturing tool.

In some embodiments, the target subject may include, or may be, a human. In some embodiments, the target subject may include, or may be, a non-human animal. The non-human animal may include, or may be, a mammal. Examples of non-human animals include, but are not limited to, working animals, livestock animals, pet animals, and wild animals.

In some embodiments, the liquid collection device includes a flow passage member. In some embodiments, the flow passage member may include a flow passage that connects one end and other end of the flow passage member. In some embodiments, the flow passage member may include a plurality of flow passages. In some embodiments, the flow passage member may include only one flow passage. In some embodiments, when the flow passage member includes a plurality of flow passages, the flow passages extend in a tube axis direction connecting the one end and the other end of the flow passage member. In some embodiments, the flow passages may or may not be substantially parallel to each other.

In some embodiments, the flow passage may include a capillary tube (also referred to as a capillary tube channel). In some embodiments, at least a portion of the flow passage may be composed of a capillary tube. In some embodiments, the flow passage may include a capillary tube at least at the one end at which the liquid is received. In some embodiments, the capillary tube may include a plurality of capillary tubes.

The term "tube axis direction" used herein refers to a direction connecting one end and the other end of the flow passage member.

In some embodiments, the flow passage member may have a columnar shape that extends in the tube axis direction connecting one end and the other end of the flow passage member. In some embodiments, the flow passage member having the columnar shape may have a plurality of grooves or only one groove that extends in the tube axis direction along an outer peripheral surface of the flow passage member. In some embodiments, the groove or grooves each serves as a flow passage for the liquid. The cross-sectional shape of the groove or grooves may be, for example, without limitation, a U-shape (the corners may be substantially right angled, obtuse angled, acute angled, or rounded), a V-shape (the corner may be substantially acute angled or rounded), or a general trough shape. In some embodiments, the flow passage may be slit-shaped. A slit or a groove that opens outward can be easily accessed from the outside. For example, processing liquid (hereinafter also referred to as a processing solution) can be easily brought into contact with the liquid in the flow passage. Accordingly, for example, the mixing is facilitated.

In some embodiments, the flow passage member may have a columnar shape that extends in the tube axis direction. In some embodiments, the flow passage member having the columnar shape may have a circular shape or an elliptical shape in cross-section when viewed in the tube axis direction. In some embodiments, the flow passage member may have, for example, a polygonal shape, such as a triangular shape, a quadrangular shape, a pentagonal shape, a hexagonal shape, or an octagonal shape in cross-section. In some embodiments, the flow passage member may have a plurality of flow passages extending therethrough in the tube axis direction to provide communication between the one end and the other end of the flow passage member. In some embodiments, the flow passage member may have a uniform cross-sectional shape in the tube axis direction (for example, a cylindrical shape) or a cross-sectional shape that varies in the tube axis direction (for example, decreases in size toward the one end).

In some embodiments, the flow passage member may be formed by bundling a plurality of single tubes that extend in the tube axis direction. In some embodiments, each single tube may have a tubular shape that extends in the tube axis direction and include a flow passage that connects one end and the other end of the single tube. In some embodiments, the single tubes may be joined together by adhesion or fusion bonding. In some embodiments, the single tubes may be bundled together with a band or the like. In some embodiments, the single tubes may be formed integrally with each other by using a resin material. When, for example, the single tubes are bundled together, holes in the single tubes and gaps between the single tubes serve as flow passages for the liquid.

In some embodiments, the flow passage may be configured to receive and contain a predetermined or quantified amount of liquid. In some embodiments, the liquid may be sucked into the flow passage by capillary action. The flow passage may include a capillary tube (channel) at least at a distal end thereof. In some embodiments, the capillary tube of the flow passage may have a predetermined length. The volume of the liquid collected in the flow passage may be determined by the length of the capillary tube. In some embodiments, the capillary tube may include a portion having a side hole. In some embodiments, capillary action occurs in a region from one end (distal end) of the capillary tube to the side hole. The amount of the liquid that is collected may be determined by the capacity of this region. The capillary tube may have a cross-sectional area that is increased at the other end or a portion thereof. Accordingly, further capillary action does not substantially occur. In some embodiments, a portion of the flow passage that is downstream of the capillary tube, that is, further away from the one end (distal end) or closer to the other end than the capillary tube, may be configured to impede capillary action.

The amount of the liquid that is collected may be determined by a region extending from the one end (distal end) and in which capillary action occurs. The amount of the liquid that is collected may be determined by the cross-sectional area and the length of the capillary tube. In some embodiments, the capillary tube may have a mark that indicates a certain amount of the liquid that is collected or scale marks used to determine the amount of the liquid that is collected.

In some embodiments, the liquid may be collected in the flow passage by a suction mechanism other than the capillary tube. For example, a mechanism, such as a pump, that is connected to the flow passage may be provided. These suction mechanisms may be used to relatively accurately collect a certain amount of the liquid.

<Tank>

In some embodiments, the tank may be configured to contain the processing solution. The tank may be filled with the processing solution when used. In some embodiments, the processing solution may be contained in the tank. In some embodiments, the processing solution may be sealed in the tank. It is not necessary that the processing solution be sealed in the tank. For example, the tank may have an opening.

In some embodiments, the tank may include a tank body. The tank body may have an inner wall that defines an inside or an internal space of the tank. In some embodiments, the tank may include the tank body and a sealing member. The tank body and the sealing member may define the inside of the tank.

At least a portion of the sealing member is configured to receive the flow passage member. The flow passage member may push the sealing member that seals the tank body into the tank to break the sealing of the tank, and then move into the tank. The sealing member may include at least two sealing members. A first one of the sealing members may be configured to receive the flow passage member. A second one of the sealing members may be configured to enable the mixed solution to be discharged from the tank.

The first and second ones of the sealing member may be fixed to the tank body so as to seal the tank body, and may be removable by an external force. For example, each sealing member may be, or may include, a bead. The bead may be fixed to the inner wall of the tank body in a mechanically removable manner. The bead may be fixed to the tank body such that the bead is removable from the fixed position by being pushed. For example, each sealing member may be, or may include, a breakable film. The film may be configured to break when a pointed member is pressed thereagainst.

In some embodiments, the flow passage member may be inserted into the tank that contains the processing solution. At this time, the liquid received in the flow passage of the flow passage member comes into contact with the processing solution. The received liquid and the processing solution start to mix with each other. The liquid and the processing solution may mix with each other naturally or by diffusion. A user may shake the liquid collection device to accelerate the mixing process. The liquid collection device may be vertically inverted, rotated about a tube axis, or vibrated by using a machine, such as a stirring device or a shaking device. The mixing process may be accelerated in this way. The bead that serves as the sealing member may move in the tank to accelerate the mixing process.

In some embodiments, the tank may be configured such that the received liquid and the processing solution are sealed therein after the flow passage member is inserted into the tank. The tank may be configured such that the inside thereof is sealed at least while the liquid and the processing solution mix with each other. The tank may be configured such that the mixed solution obtained by the mixing of the received liquid and the processing solution is sealed therein. For example, the tank may have a lid. The lid may be closed to seal the mixed solution in the tank. For example, the internal space of the tank may be sealed by the inserted flow passage member and the tank.

In some embodiments, a container for receiving the mixed solution discharged from the device may be provided. The mixed solution may be sealed in the internal space of the tank or the container for transportation or storage thereof.

The capacity of the capillary tube (or a portion of the flow passage that receives the liquid; the same applies hereinafter) may be greater than or equal to, for example, 1 μL, 2 μL, 3 μL, 4 μL, 5 μL, 6 μL, 7 μL, 8 μL, 9 μL, 10 μL, 15 μL, 20 μL, 25 μL, or the like. The capacity of the capillary tube may be smaller than or equal to, for example, 100 μL, 90 μL, 80 μL, 70 μL, 60 μL, 50 μL, 40 μL, 35 μL, 30 μL, 25 μL, 20 μL, 15 μL, 10 μL or the like. The capacity of the capillary tube may be between 5 μL and 30 μL. The capacity of the capillary tube may be between 10 μL and 20 μL.

The capacity of the tank (or the volume of the liquid (processing solution) contained in the tank; the same applies hereinafter) may be greater than or equal to, for example, 10 μL, 20 μL, 25 μL, 30 μL, 35 μL, 40 μL, 45 μL, 50 μL, or the like. The capacity of the tank may be smaller than or equal to, for example, 5 mL, 3 mL, 2 mL, 1 mL, 500 μL, 400 μL, 300 μL, 250 μL, 200 μL, 150 μL, 100 μL, 50 μL, or the like. The capacity of the tank may be between 2 times and 50 times the capacity of the capillary tube, or between 2 times and 20 times the capacity of the capillary tube. The dilution ratio may be 2 times to 20 times, or 2 times to 50 times. The capacity of the tank may be, for example, but not limited to, substantially 25 μL or substantially 250 μL.

<Processing Solution>

In some embodiments, the processing solution may be a diluent. The diluent may be used to dilute the received liquid. The processing solution may be liquid (preprocessing solution) used to perform a predetermined process (preprocessing) before a measurement performed on the received liquid.

The processing solution may be water or an aqueous solution. The processing solution may be a buffer. The processing solution may be, for example, a Good's buffer. The processing solution may be saline. The processing solution may be an organic solvent.

When, for example, a measurement target is a protein or the like that is sensitive to pH or salt concentration, a buffer, such as saline or a Good's buffer, may be used. When, for example, a processing target is a small molecule, such as an amino acid, buffering may be unnecessary. In such a case, water or other aqueous solutions or an organic solvent may be used. The processing solution may include an additive, such as a stabilizer or a preservative. An additive for maintaining the structure of a protein, for example, may be used.

In some embodiments, an osmotic pressure of the processing solution may be adjusted. For example, when serum is to be separated, the processing solution may have an osmotic pressure equal to the osmotic pressure of human body fluid (285±5 m Osm/L) (isotonic solution). When the osmotic pressure is low (hypotonic solution), hemolysis, which is rupturing of red blood cells, may occur. When the osmotic pressure is high (hypertonic solution), there is a possibility that the separation performance of a blood cell separation filter will be affected. In addition, there is also a possibility that a target substance will be excessively extracted from the blood cells and the measurement result will be affected as a result.

In some embodiments, the processing solution may include a stabilizer for the target substance. For example, a stabilizer for the structure of a protein may be used. The protein may be, for example, but not limited to, albumin. For example, a stabilizer may be used to stabilize the albumin structure. When a stabilizer is used, indicator molecules, such as BCP, may be caused to bind specifically at predetermined sites. When electric charges at or around the binding sites and the environment of amino acid side chains are appropriate, the indicators, for example, easily bind to the protein, and specificity is maintained. Examples of the stabilizer for the protein include, but are not limited to, saccharide, polysaccharide, salt and the like.

The processing solution may include, for example, a substance that solubilizes or dissolves mucins in saliva. In such a case, the viscosity of the body fluid, such as saliva, can be reduced.

The processing solution may include a substance (inhibitor) that inhibits a reaction involving the target substance. For example, saliva includes digestive enzymes, such as amylase. A substance that inhibits the activity of the digestive enzymes may be used.

The processing solution may include a substance (aggregating agent) that causes aggregation of a substance included in the target liquid. For example, the target liquid may include an aggregating agent that causes aggregation of, for example, fine dust, blood cells, mucins, membrane proteins, or fat. These substances may be caused to aggregate into large clumps. The clumps generated by the aggregation can be easily removed in a subsequent filtering process.

The processing solution may include a substance that dissolves or solubilizes a substance, causes aggregation of the substance, or inhibits or accelerates a reaction of the substance.

A component of the processing solution may be selected from a group composed of saline, HEPES, TES, MES, tricine, and PBS. A component of the processing solution may include a Good's buffer (for example, HEPES, TES, MES, or tricine). The processing solution may include a reference material used in a subsequent measurement.

<Pump>

In some embodiments, the pump may include a syringe. The syringe generally includes a piston and a cylinder. The syringe may be manually driven. The syringe may be mechanically driven. The form of the pump is not limited to a syringe. The pump may include an electric pump.

In some embodiments, the pump is capable of applying a pressure to the inside of the tank. In some embodiments, the pump is capable of injecting air into the tank from the outside.

In some embodiments, the pump may include a pipette valve. In some embodiments, the pipette valve may be additionally provided on the syringe. The pipette valve may be used to apply the pressure to the inside of the tank together with the syringe.

The pump may be configured to apply the pressure at or in the flow passage. The pump may be configured to apply the pressure to the inside of the flow passage at one of two ends of the flow passage. The pump may directly apply the pressure to the flow passage. The pump may apply the pressure to the inside of the tank to thereby apply the pressure to the inside of the flow passage.

The pressure applied by the pump may be a positive pressure or a negative pressure. The pressure may be varied with time. A positive pressure and a negative pressure may be applied in a temporally alternating manner.

<Discharge Channel>

In some embodiments, the device may include a discharge channel (also referred to as a discharge flow passage or a discharge path) for discharging the mixed solution to the outside. The device may include a discharge channel member including the discharge channel. In the following description, the discharge channel may mean a discharge channel member unless there is a conflict.

In some embodiments, the discharge channel may be disposed on the tank. The tank may include the discharge channel. The discharge channel may be attached to the tank. The discharge channel may be removably attached to the tank. The discharge channel may be in fluid communication with the tank. The discharge channel may be fixed to the tank. The discharge channel may be formed as a portion of the tank by integral molding.

In some embodiments, the pump may be configured to apply a pressure at the other end of the flow passage so that at least a portion or substantially the entirety of the mixed solution, the processing solution, or the liquid in the flow passage is discharged from the flow passage. When the tank is sealed, the pressure is applied also to the inside of the tank. The mixed solution in the tank may be discharged to the outside through the discharge channel by the pressure.

In some embodiments, the discharge channel may be disposed at the other end of the flow passage (end opposite to the end at which the liquid is received). The discharge channel may be in fluid communication with the other end of the flow passage. The discharge channel may be configured to be removably attachable to the flow passage member. The discharge channel may be fixed to the flow passage member. The discharge channel may be formed as a portion of the flow passage member by injection molding. Accordingly, the mixed solution flows through the flow passage and is discharged through the discharge channel. Accordingly, for example, the liquid remaining in the flow passage may be washed away in the discharging process. The liquid in the capillary tube may be washed by the mixed solution.

In some embodiments, the discharge path for the mixed solution may have a second internal space. This space may be used for further mixing of the mixed solution. Thus, the mixed solution that is temporarily discharged from the first internal space can be further mixed in the second internal space. The mixing in the first internal space may be insufficient. The flow through the discharge path and the flow or diffusion in the second internal space, for example, contribute to sufficient mixing of the received liquid and the processing solution. The received liquid and the processing solution can be sufficiently mixed in the second internal space. The second internal space may be in fluid communication with an outlet of the device. Accordingly, the mixed solution flows out from the second internal space and is discharged through the outlet. In some embodiments, the second internal space may be disposed between the first internal space and a filter in the discharge channel.

<Filter>

In some embodiments, a filter may be disposed in the discharge path for the mixed solution. In some embodiments, the filter may be capable of separating a predetermined substance (separation filter).

In some embodiments, the filter may include a plasma separation filter or a serum separation filter. The filter may include a plasma separation filter (or membrane) that receives blood and captures cellular components while allowing plasma to pass therethrough. The filter may include a serum separation filter (or membrane) that receives blood and captures clots while allowing serum to pass therethrough.

The filter may include a filter that separates other substances. For example, the filter may be capable of removing fine dust. For example, the filter may be capable of removing macromolecular substances, such as mucins. For example, the filter may be capable of removing proteins or the like that have aggregated due to the effect of the processing solution. For example, a substance capable of reacting with a substance that passes through the filter may be supported by the filter. For example, an antibody may be supported by the filter. For example, a substance capable of binding to a protein may be supported by the filter. For example, a surface of the filter (for example, surfaces of filter fibers) may be composed of a substance having a high affinity for a predetermined substance. In such a case, the predetermined substance may be adsorbed to the surface of the filter.

In some embodiments, the filter may be a fibrous material. The filter may be a woven fabric or a nonwoven fabric. In some embodiments, the filter may be a porous material.

The filter may be a fibrous material composed of, for example, cellulose, glass, or a macromolecular material. The material of the filter may be selected from a group composed of cellulose, glass, and polymers.

Embodiment 1

FIGS. 1A to 1F illustrate the structure of a liquid collection device according to an embodiment in steps in which the liquid collection device is used. The liquid collection device illustrated in FIGS. 1A to 1F extends in a tube axis direction, and includes members assembled together in the tube axis direction.

As illustrated in FIG. 1A, a flow passage member 110 includes a flow passage 111 that extends therethrough in the tube axis direction, and is capable of receiving liquid at one end (distal end) thereof. The flow passage 111 extends in a longitudinal direction of the flow passage member 110. The flow passage 111 serves as a capillary tube at a distal end thereof. The flow passage 111 has a side hole 112. A distal end 113 of the flow passage is brought into proximity to or contact with liquid 102 on a target 101. The liquid 102 flows upward through the capillary tube 111 from the distal end by capillary action. The liquid 102 stops at the position of the side hole 112, and is not sucked upward beyond the side hole 112 (see FIG. 1C).

Figure 1B:
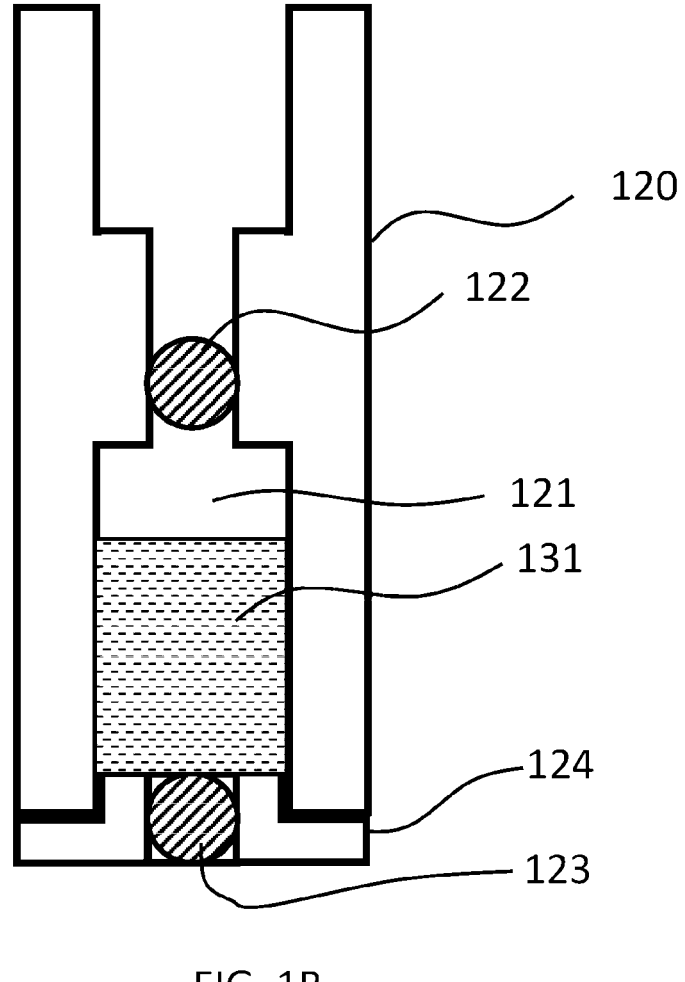
FIG. 1B is a sectional view illustrating the process of using the liquid collection device according to the embodiment.

As illustrated in FIG. 1B, the tank 120 has an internal space 121 in which processing solution 131 is contained. The internal space 121 is sealed at both sides thereof in the tube axis direction by two sealing members (beads in FIG. 1B) 122 and 123. The bead 122 is fitted to an upper opening in the upper section of FIG. 1B. A stopper 124 is fitted to the tank 120 in the lower section of FIG. 1B. The bead 123 is fitted to an opening in the stopper 124. The processing solution 131 is sealed in the internal space 121 of the tank 120 by the beads 122 and 123.

Figure 1C:
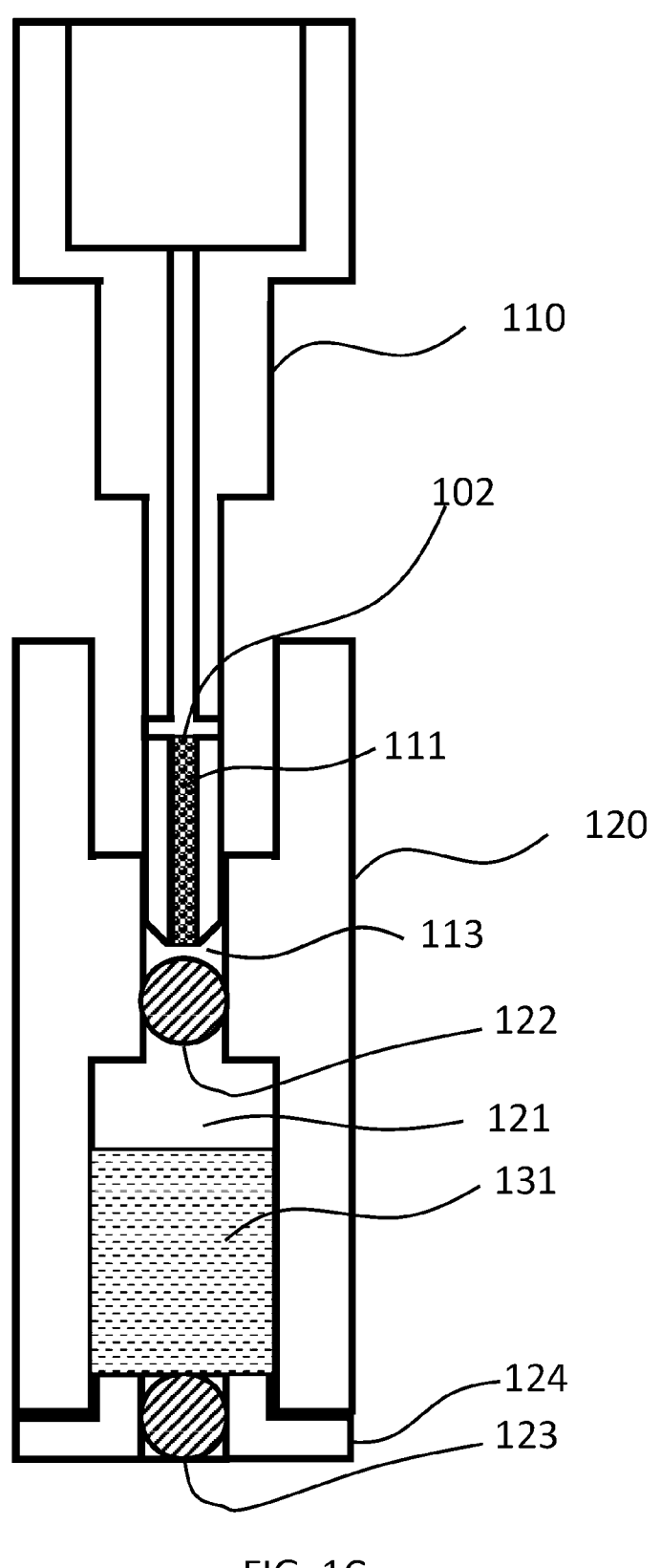
FIG. 1C is a sectional view illustrating the process of using the liquid collection device according to the embodiment.

Next, as illustrated in FIG. 1C, the flow passage member 110 in which the liquid 102 is received and contained in the capillary tube 111 is inserted into the tank 120. The flow passage member 110 is inserted into the tank 120 from the distal end 113 of the capillary tube 111. The distal end of the flow passage member 110 pushes the sealing member 122 so that the sealing member 122 falls into the internal space 121 of the tank.

Figure 1D:
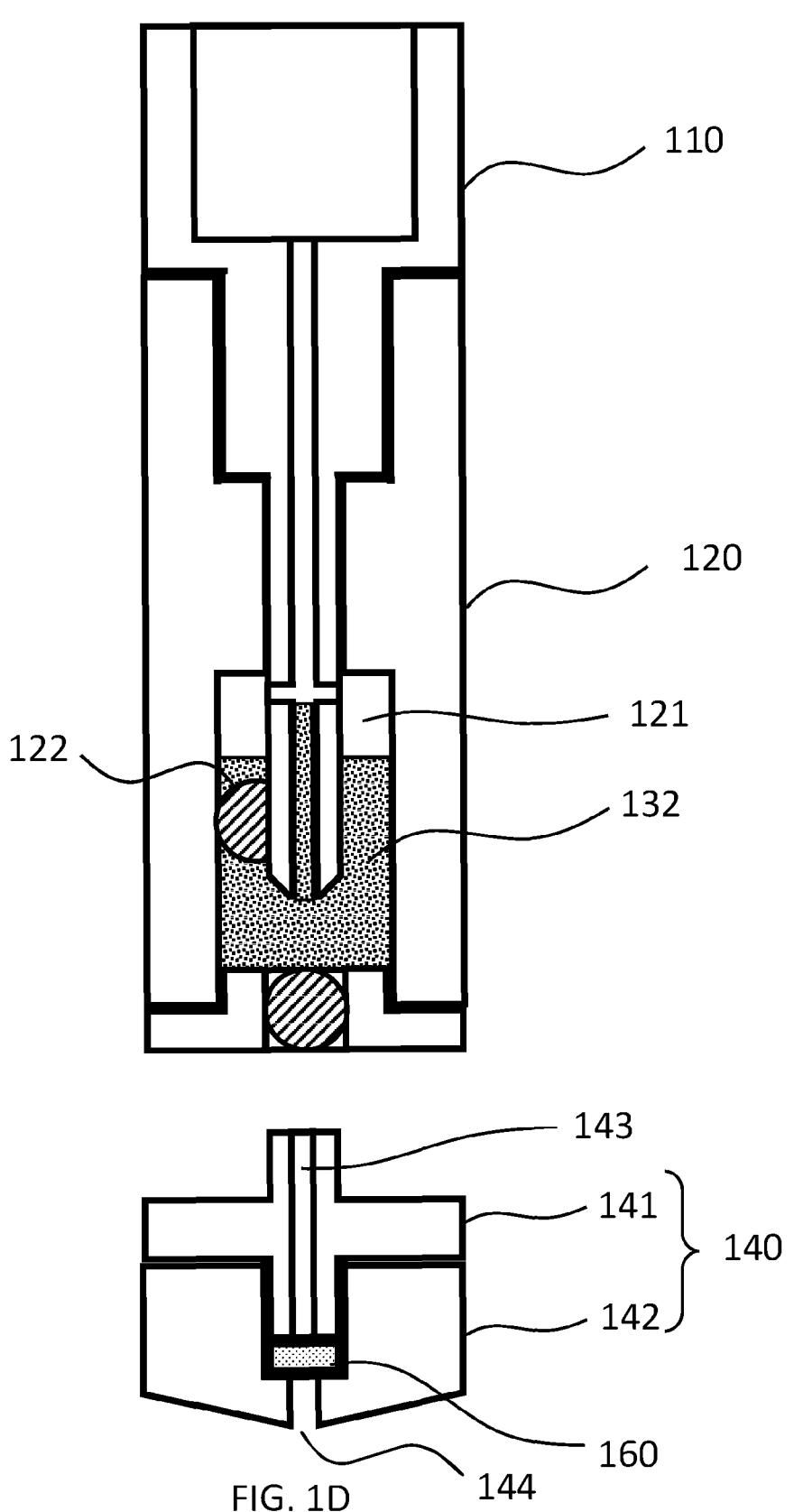
FIG. 1D is a sectional view illustrating the process of using the liquid collection device according to the embodiment.

The liquid 102 received and contained in the flow passage comes into contact with the preprocessing solution 131 contained in the internal space 121 of the tank. Accordingly, the liquid 102 and the preprocessing solution 131 mix with each other so that a mixed solution 132 is generated (FIG. 1D). The liquid 102 and the preprocessing solution 131 may mix with each other by diffusion. The mixing may be accelerated by a movement of the bead 122.

As illustrated in FIG. 1D, a discharge channel member 140 is provided. The discharge channel member 140 illustrated in FIG. 1D includes a first discharge channel member 141 and a second discharge channel member 142. The first discharge channel member 141 is inserted into the internal space 121 of the tank and has a discharge channel 143 through which the mixed solution 132 is discharged. The second discharge channel member 142 has an outlet 144. The first discharge channel member 141 and the second discharge channel member 142 are combined together with a filter 160 interposed therebetween at an intermediate location of the discharge channel 143.

One end of the discharge channel 143 in the first discharge channel member 141 of the discharge channel member 140 is inserted into the internal space 121 of the tank through the lower stopper 124 of the tank 120.

Figure 1E:
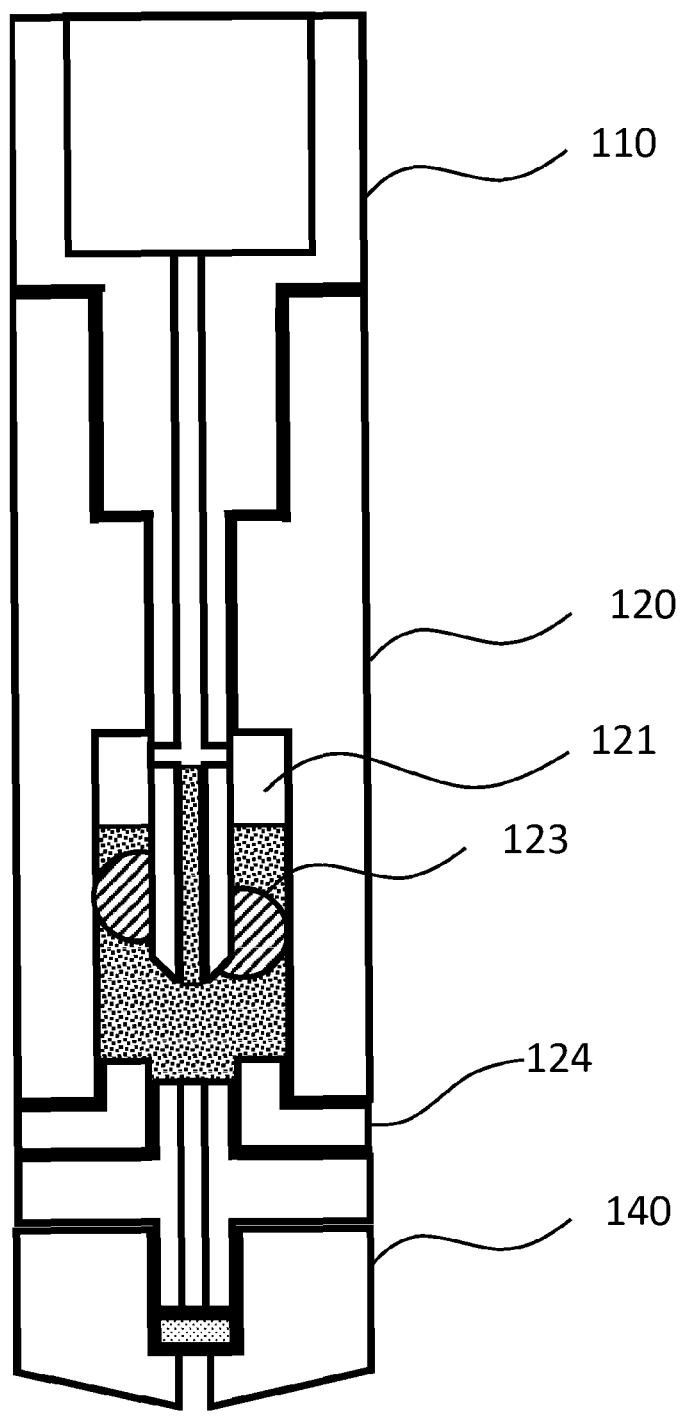
FIG. 1E is a sectional view illustrating the process of using the liquid collection device according to the embodiment.

As a result, as illustrated in FIG. 1E, the discharge channel member 140 is combined with the tank 120. The bead 123 is pushed into the internal space 121 of the tank.

The liquid 102 received and contained in the flow passage comes into contact with the preprocessing solution 131 contained in the internal space 121 of the tank. Accordingly, the liquid 102 and the preprocessing solution 131 mix with each other so that the mixed solution 132 is generated. The liquid 102 and the preprocessing solution 131 may mix with each other by diffusion. The mixing may be accelerated by a movement of the bead 122.

In this state, the flow passage member 110 is fitted to the tank 120 in a sealed manner. The discharge channel member 140 is also fitted to the tank 120 in a sealed manner. The internal space 121 of the tank 120 is sealed by the flow passage member 110 and the discharge channel member 140. The mixed solution 132 is contained in the internal space 121 that is sealed.

Figure 1F:
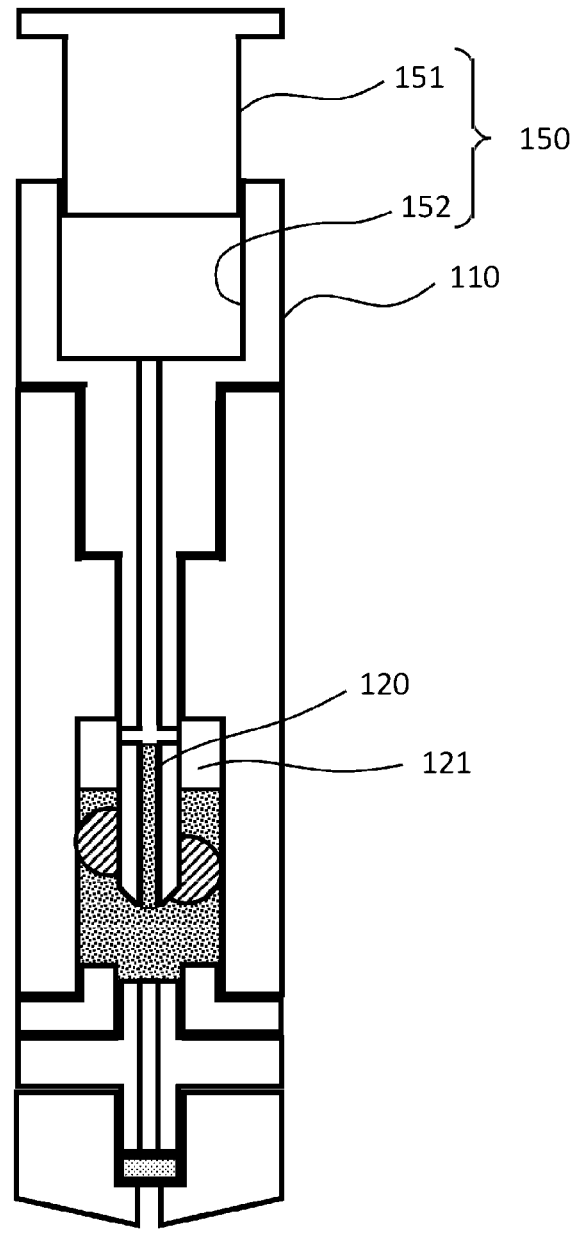
FIG. 1F is a sectional view illustrating the process of using the liquid collection device according to the embodiment.

As illustrated in FIG. 1F, a cylinder 152 is formed at an upper end of the flow passage member 110 (end opposite to the end at which the capillary tube 120 is provided). A piston 151 is fitted to the cylinder 152. The piston 151 and the cylinder 152 form a syringe 150. The syringe 150 has a function of a pump and is capable of applying a pressure to the capillary tube 120 and to the sealed internal space 121 through the capillary tube 120, the capillary tube 120 and the sealed internal space 121 being in fluid communication with each other.

Figure 1G:
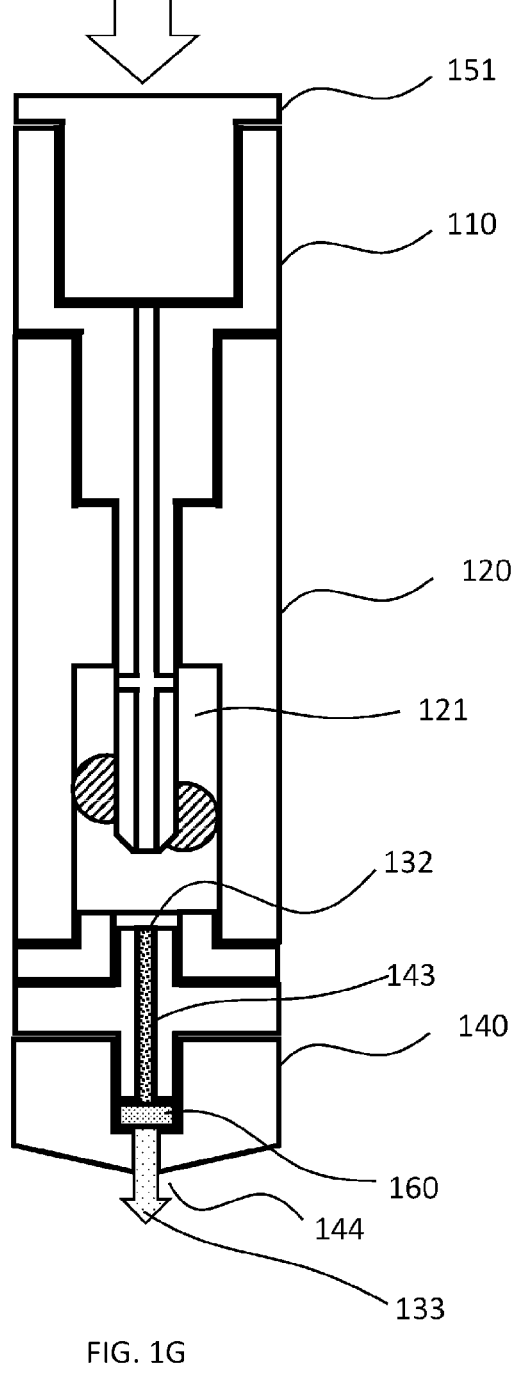
FIG. 1G is a sectional view illustrating the process of using the liquid collection device according to the embodiment.

As illustrated in FIG. 1G, when the piston 151 is pushed, the mixed solution in the sealed internal space 121 of the tank 120 flows through the discharge channel 143 to the filter 160. The mixed solution 132 is filtered by the filter 160. A filtered solution 133 is discharged to the outside through the outlet 144 of the discharge channel 143.

Embodiment 2

FIGS. 2A to 2D illustrate the structure of a liquid collection device according to an embodiment in steps in which the liquid device is used. The liquid collection device illustrated in FIGS. 2A to 2D extends in a tube axis direction, and includes parts assembled together in the tube axis direction.

Figure 2A:
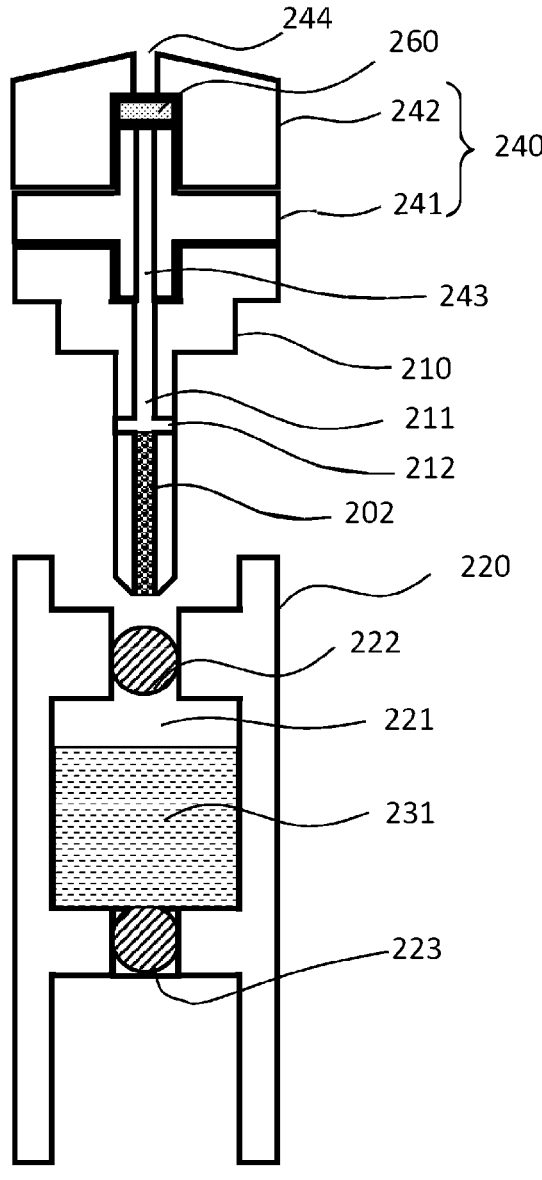
FIG. 2A is a sectional view illustrating a process of using a liquid collection device according to an embodiment.

As illustrated in FIG. 2A, the flow passage member 210 includes a flow passage 211 that extends therethrough in the tube axis direction. The flow passage 211 serves as a capillary tube at one end thereof, and has a side hole 212. The capillary tube is capable of receiving a specific amount of liquid 202 in the space between the distal end and the side hole 212. In FIG. 2, the liquid 202 is already received in the flow passage member 210.

In the embodiment illustrated in FIGS. 2A to 2D, a discharge channel member 240 is connected to the flow passage member 210. The flow passage 211 of the flow passage member 210 is in fluid communication with a discharge channel 243 of the discharge channel member 240 at the other end of the flow passage 211 (end opposite to the distal end at which the target liquid 202 is received).

The discharge channel member 240 illustrated in FIG. 2A includes a first discharge channel member 241 and a second discharge channel member 242. The first discharge channel member 241 is fitted to the flow passage member 210 and has a discharge channel 243 through which a mixed solution 232 (see, for example, FIG. 2C) is discharged. The second discharge channel member 242 has an outlet 244. The first discharge channel member 241 and the second discharge channel member 242 are combined together with a filter 260 interposed therebetween at an intermediate location of the discharge channel 243.

As illustrated in FIG. 2A, the tank 220 has an internal space 221 in which processing solution 231 is contained. The internal space 221 of the tank 220 is sealed at both sides thereof in the tube axis direction by two sealing members (beads in FIG. 2A) 222 and 223. The bead 222 is fitted to an upper opening in the upper section of FIG. 2A. The bead 223 is fitted to a lower opening in the lower section of FIG. 2A. The processing solution 231 is sealed in the internal space 221 of the tank 220 by the beads 222 and 223.

Figure 2B:
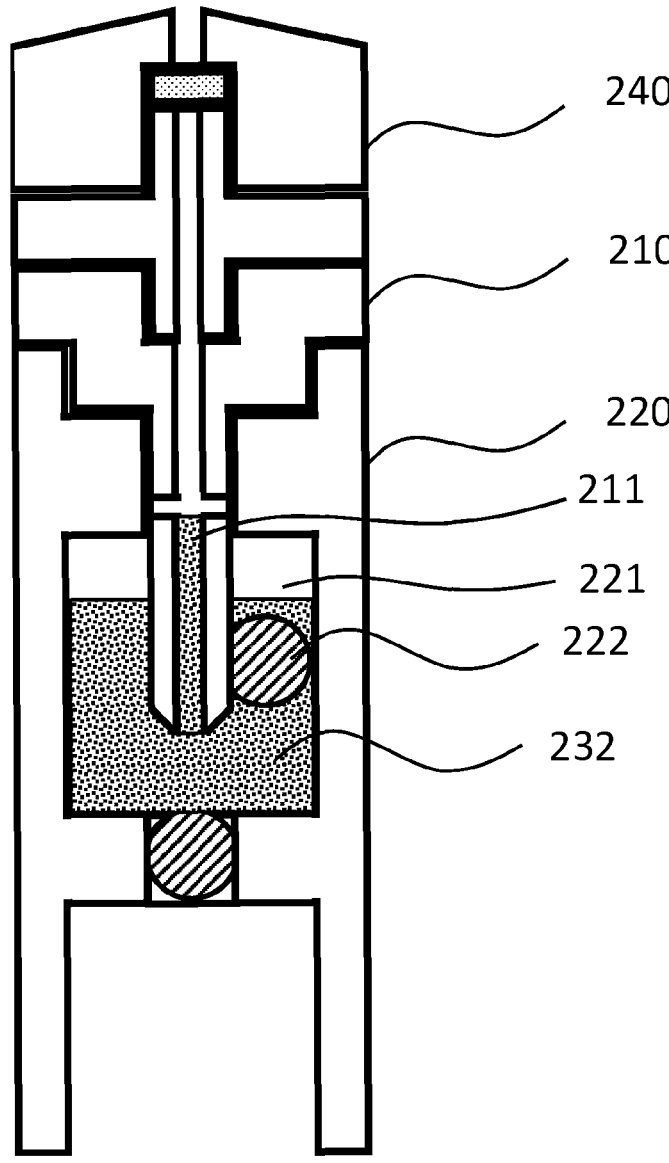
FIG. 2B is a sectional view illustrating the process of using the liquid collection device according to the embodiment.

Next, as illustrated in FIGS. 2A and 2B, the flow passage member 210 in which the liquid 202 is received and contained in the capillary tube 211 is inserted into the tank 220. The flow passage member 210 is inserted into the tank 220 from the distal end of the capillary tube 211. The distal end of the flow passage member 210 pushes the sealing member (bead) 222 so that the sealing member (bead) 222 falls into the internal space 221 of the tank.

The liquid 202 received and contained in the flow passage comes into contact with the preprocessing solution 231 contained in the internal space 221 of the tank. Accordingly, the liquid 202 and the preprocessing solution 231 mix with each other so that the mixed solution 232 is generated (FIG. 2B). The liquid 202 and the preprocessing solution 231 may mix with each other by diffusion. The mixing may be accelerated by a movement of the bead 222. The tank 220 may be shaken or rotated, and the flow passage member 210 may be moved with respect to the tank 220. For example, the flow passage member 210 may be extracted from the tank 220 and then inserted into the tank 220 again, or be repeatedly extracted from and inserted into the tank 220. The flow passage member 210 may be rotated with respect to the tank 220.

Figure 2C:
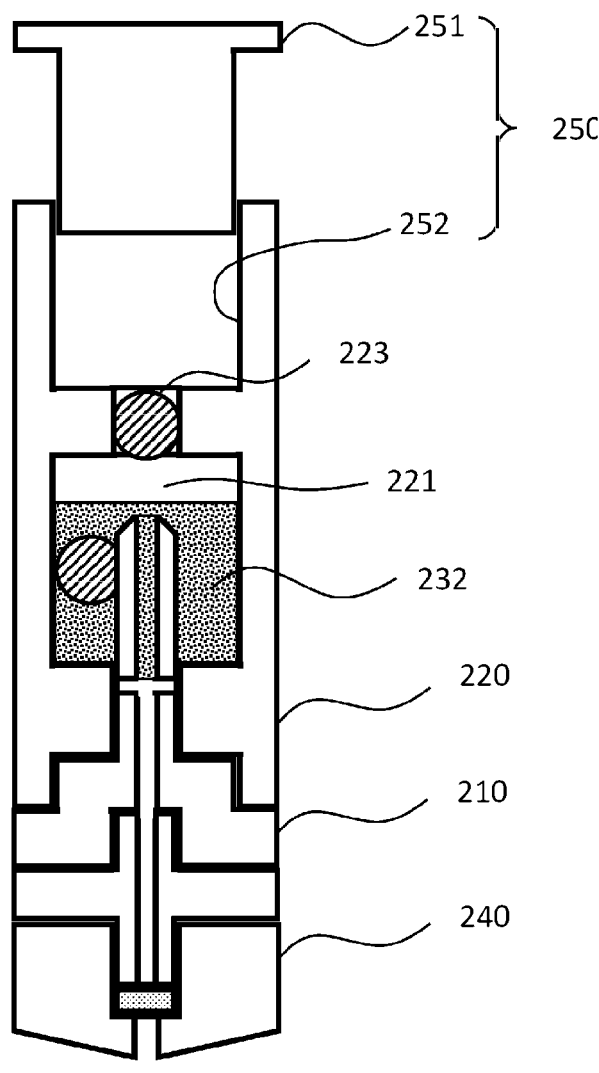
FIG. 2C is a sectional view illustrating the process of using the liquid collection device according to the embodiment.

As illustrated in FIG. 2C, the tank 220, the flow passage member 210, and the discharge channel member 240 that are fitted together are vertically inverted.

In this state, the flow passage member 210 is fitted to the tank 220 in a sealed manner. The discharge channel member 240 is fitted to the tank 220. The internal space 221 of the tank 220 is defined by the flow passage member 210 and the second bead 223. The mixed solution 232 is contained in the internal space 221.

As illustrated in FIG. 2C, a cylinder 252 is formed at an upper end of the tank 220 (end opposite to the end having an opening through which the capillary tube 211 is inserted). A piston 251 is fitted into the cylinder 252. The piston 251 and the cylinder 252 form a syringe 250. The syringe 250 has a function of a pump and is capable of applying a pressure to the inside of the syringe 250 and the internal space 221 that is sealed.

Figure 2D:
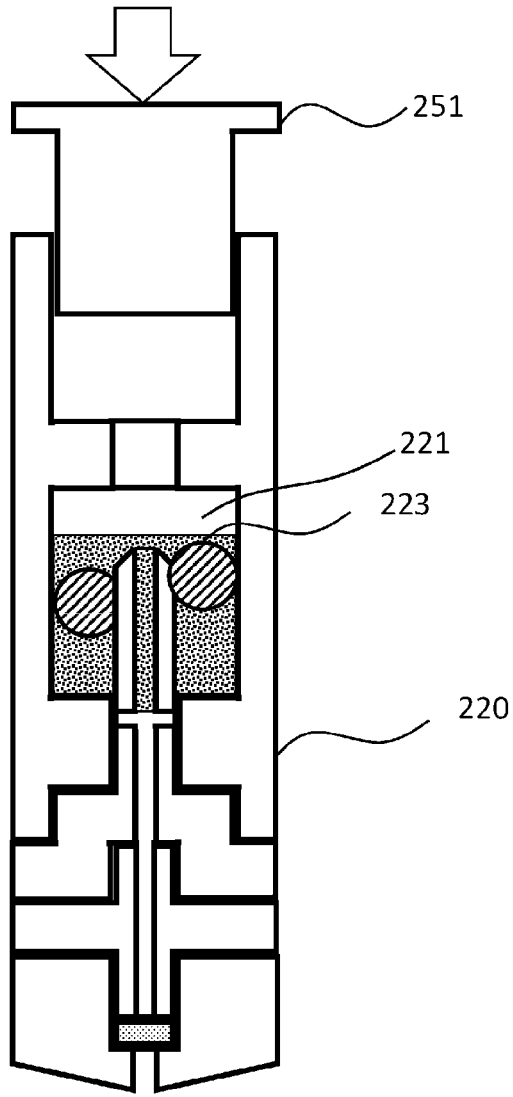
FIG. 2D is a sectional view illustrating the process of using the liquid collection device according to the embodiment.

As illustrated in FIG. 2D, the piston 251 is pushed with respect to the tank 220 in an axial direction to generate a pressure that pushes the bead 223. The bead 223 falls into the internal space 221 of the tank.

Figure 2E:
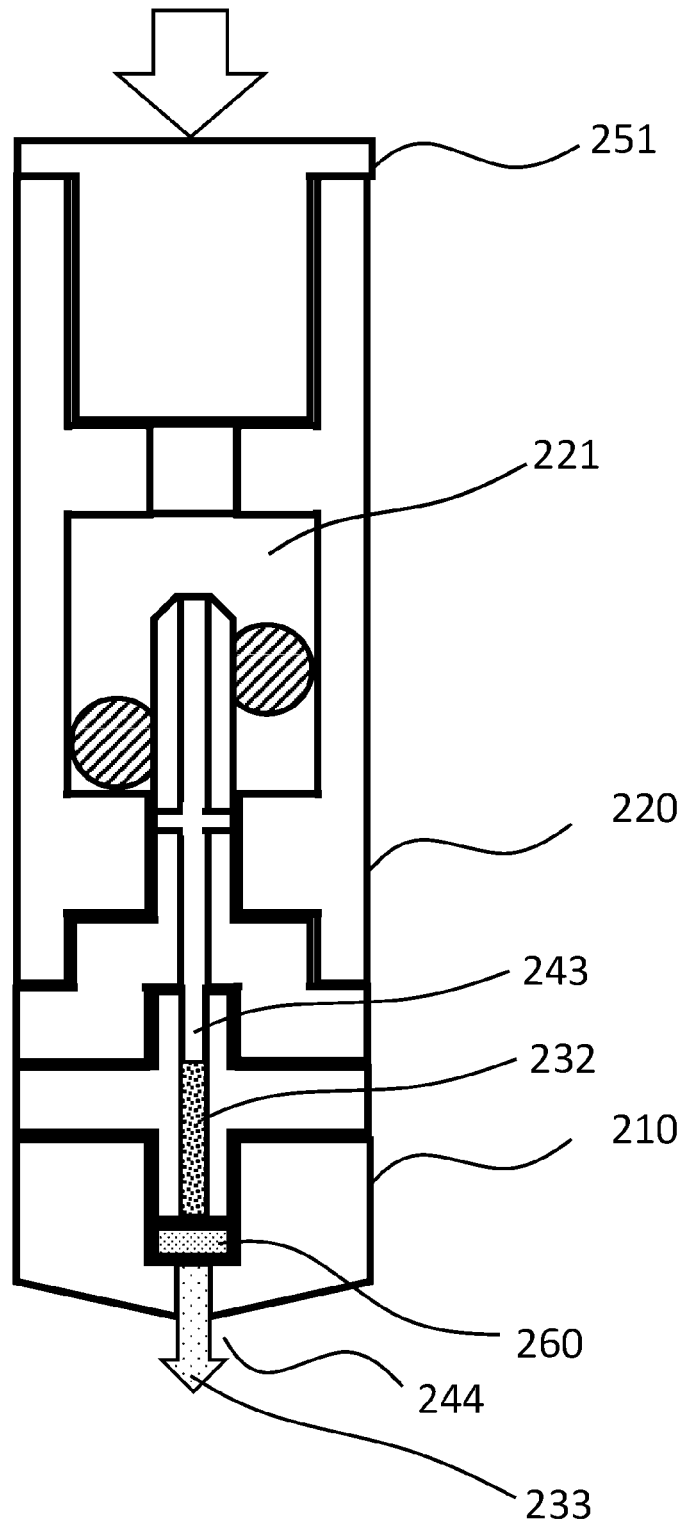
FIG. 2E is a sectional view illustrating the process of using the liquid collection device according to the embodiment.

As illustrated in FIG. 2E, when the piston 251 is further pushed, the mixed solution 232 in the sealed internal space 221 of the tank 220 flows through the discharge channel 243 to the filter 260. The mixed solution 232 is filtered by the filter 260. A filtered solution 233 is discharged to the outside through the outlet 244 of the discharge channel 243.

<Filter>

The present disclosure provides a flow passage having a filter (also referred to as a filter flow passage, a filter flow passage member, or a filter flow passage device; name is not limited to these examples). The filter flow passage may be included in the liquid collection device according to the present disclosure. The filter flow passage may be included in other flow passage devices. The present disclosure provides a flow passage device including a filter.

In some embodiments, the filter is disposed in a flow passage. The filter generally receives liquid that flows through the flow passage and blocks or removes a predetermined substance. The filtered liquid is discharged through the flow passage. The liquid in the filter may reach a circumferential surface (hereinafter also referred to as an outer surface) of the filter in a direction perpendicular to a flow-passage direction of the filter. The filter or the filter flow passage may be configured such that the liquid that flows into and through the filter does not reach the outer surface of the filter. The liquid that has reached the outer surface of the filter may flow along an inner wall of the flow passage. The liquid that flows along the inner wall of the filter is substantially not filtered by the filter. Therefore, it is important to prevent the liquid from reaching the outer surface of the filter and cause the liquid to pass through the filter.

<Filter Type 1>

Figure 3:
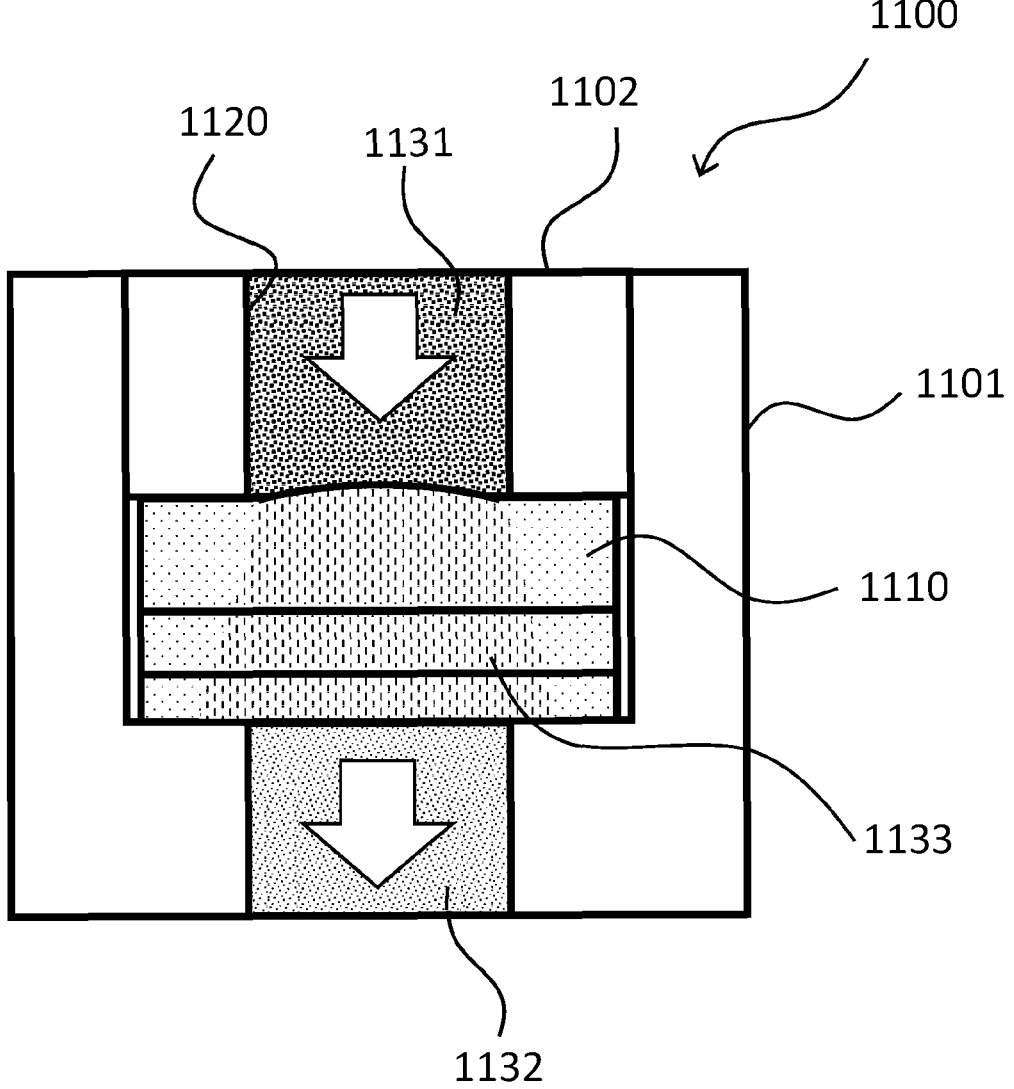
FIG. 3 is a sectional view of a filter flow passage according to an embodiment.

FIG. 3 illustrates a filter flow passage (device) 1100 according to an embodiment. The filter flow passage 1100 includes a first flow passage member 1101, a second flow passage member 1102, and a filter 1110 fixed therebetween. The first flow passage member 1101 and the second flow passage member 1102 both have a tubular shape. The second flow passage member 1102 is inserted in and fitted to the first flow passage member 1101 in an axial direction. The first flow passage member 1101 and the second flow passage member 1102 are coaxially assembled together in a flow direction (direction of arrows in FIG. 3).

The first flow passage member 1101 and the second flow passage member 1102 define a flow passage 1120 and a space whose radial size is greater than that of the flow passage 1120 in cross section and in which the filter 1110 is disposed. The second flow passage member 1102 has an end portion having a circular or concentric circular shape when viewed in the axial direction. The end portion has an end surface that is perpendicular to the axial direction. The circular end portion is in contact with an outer peripheral portion of a surface of the filter 1110 that is perpendicular to the axial direction.

Unfiltered liquid 1131 flows through the flow passage 1120 and is absorbed into the filter 1110. The liquid 1131 is filtered by flowing through the filter. Filtered liquid 1132 is discharged through the flow passage 1120. As illustrated in FIG. 3, in some embodiments, a portion of the flow passage in which the filter is disposed may have a diameter greater than the diameter of other portions of the flow passage. The filter disposed in this portion may have a diameter greater than the diameter of the flow passage.

The diameter of the flow passage 1120 is sufficiently less than that of the filter 1110. Therefore, the liquid that flows into the filter 1110 does not reach the outer surface of the filter 1110. The unfiltered liquid 1131 is absorbed into the filter 1110 through an upstream surface of the filter 1110 and flows through the filter 1110 while being filtered. The filter flow passage 1100 is designed so that liquid 1133 in the filter does not reach the outer periphery of the filter 1110 (inner peripheral surface of the first flow passage member 1101 in FIG. 3).

In some embodiments, the second flow passage member 1102 may be pressed toward the first flow passage member 1101. In some embodiments, an outer peripheral portion of the filter 1110 may be compressed in the flow direction. In such a case, the possibility that the liquid will flow through the filter in a direction toward the outer surface can be eliminated or reduced.

<Filter Type 2>

In some embodiments, the filter may have a circumferential end surface that is substantially not in contact with an inner wall of the flow passage at least at a portion of the flow passage in the flow direction. The filter may be configured such that the filter is not in contact with the inner wall of the flow passage over the entire circumference thereof. In some embodiments, the filter may be configured such that the circumferential end surface thereof is substantially not in contact with the inner wall of the flow passage at least at a portion of the flow passage in the flow direction.

Figure 4:
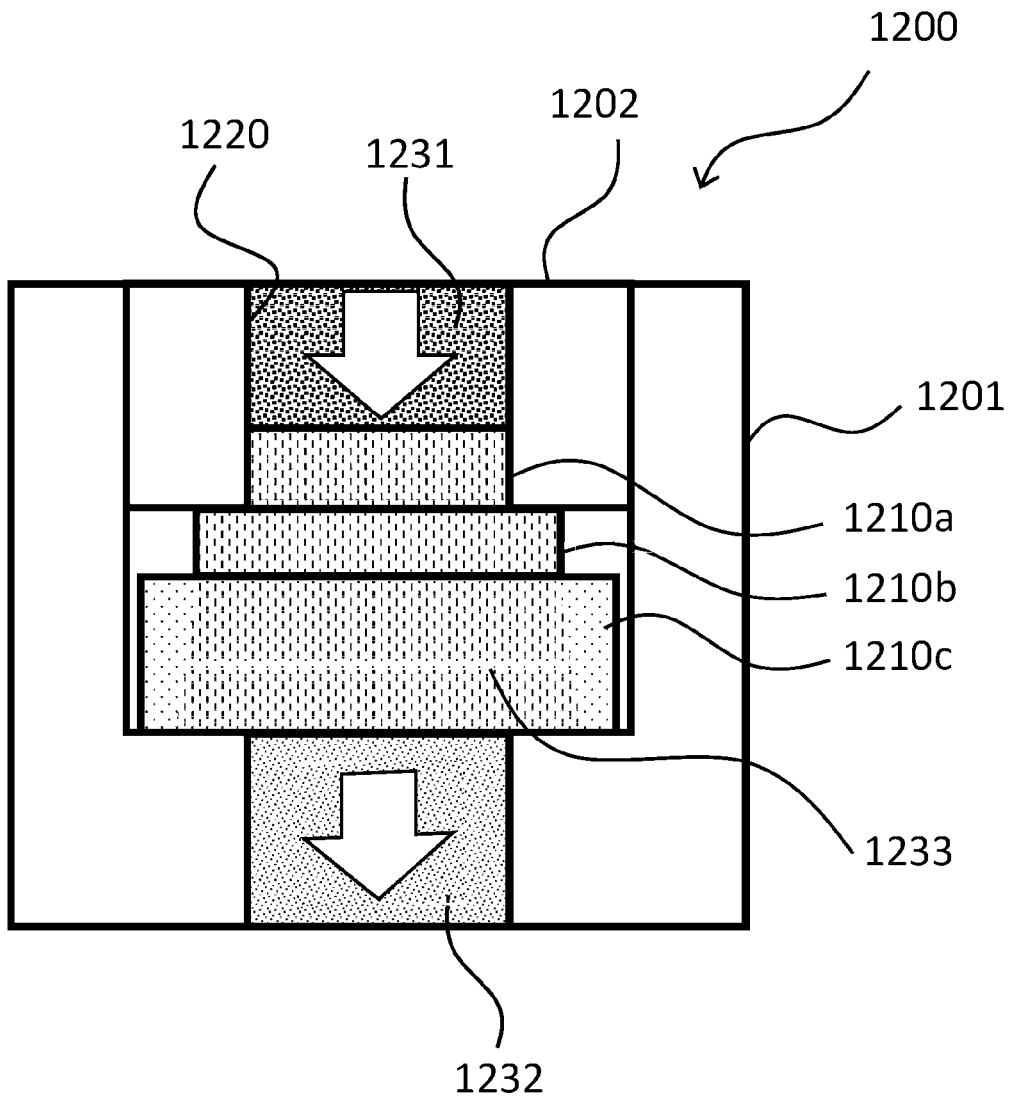
FIG. 4 is a sectional view of a filter flow passage according to an embodiment.

FIG. 4 illustrates a filter flow passage (device) 1200 according to an embodiment. The filter flow passage 1200 includes a first flow passage member 1201, a second flow passage member 1202, and three filters 1210a, 1210b, and 1210c. The filters 1210a, 1210b, and 1210c are not necessarily disposed or fixed between the first flow passage member 1201 and the second flow passage member 1202. The first flow passage member 1201 and the second flow passage member 1202 both have a tubular shape. The second flow passage member 1202 is inserted in and fitted to the first flow passage member 1201 in an axial direction. The first flow passage member 1201 and the second flow passage member 1202 are coaxially assembled together in a flow direction.

The first flow passage member 1201 and the second flow passage member 1202 define a flow passage 1220 and a space whose radial size is greater than that of the flow passage 1220 in cross section and in which the filters 1210b and 1210c are disposed. The second flow passage member 1202 has an end portion having a circular or concentric circular shape when viewed in the axial direction. The end portion has an end surface that is perpendicular to the axial direction. The circular end portion is in contact with an outer peripheral portion of a surface of the second filter 1210b that is perpendicular to the axial direction.

The first filter 1210a is disposed in the first flow passage member 1201, and is configured to absorb substantially all of liquid 1231 that flows through the flow passage 1220. The first filter 1210a is in contact with the second filter 1210b. Accordingly, substantially all of the liquid that flows out of the first filter 1210a is absorbed by the second filter 1210b.

The outer surface of the second filter 1210b is not in contact with an inner wall of the flow passage 1220. Therefore, liquid 1233 that reaches the outer surface of the second filter 1210b is prevented from reaching and flowing along the inner wall of the flow passage 1220.

In some embodiments, the first filter 1210a may be omitted, and the filter 1210 may include only the second filter 1210b and the third filter 1210c.

The second filter 1210b is disposed in contact with the third filter 1210c in a region inside an outer periphery of the third filter 1210c. An outer periphery of the second filter 1210b is in contact with the third filter 1210c in a region inside the outer periphery of the third filter 1210c. When viewed from the upstream side in the axial direction, no part of the second filter 1210b protrudes outward from the outer periphery of the third filter 1210c, and the second filter 1210b is disposed sufficiently inward from the outer periphery of the third filter 1210c. Accordingly, for example, the possibility that the liquid will reach the outer surface of the third filter 1210c can be eliminated or reduced. The liquid 1231 that reaches the filters flows through the filters without coming into contact with the inner wall of the flow passage 1220. The liquid 1233 in the filters is subjected to a predetermined filtering process. Filtered liquid 1232 is discharged to the outside from the filter 1210c.

As described above with regard to filter types 1 and 2, it is important that the filters absorb all of the liquid that flows and that the liquid be prevented from passing through the filter region without being subjected to a predetermined filtering effect. Accordingly, for example, each filter may have a portion that is constricted with respect to the inner wall of the flow passage at a portion of the filter in the flow direction.

A filter having a large area may be used to filter a large amount of liquid. In contrast, when a small amount of liquid is to be filtered, the flow passage and the filter are required to have a small cross-sectional area and/or a small volume. Some embodiments of the present disclosure provide a filter flow passage having a small flow passage and a small filter capacity. Accordingly, for example, satisfactory filtering performance can be obtained, and the amount of liquid that remains in the filter can be minimized.

The present disclosure also provides the following embodiments:

A001
A device that collects liquid, the device comprising:
a flow passage member including a flow passage that receives liquid at one end of the flow passage and that is capable of containing the received liquid;
a tank having an internal space in which a processing solution is contained, the tank being configured to receive at least one end of the flow passage member and allow mixing of the processing solution contained in the tank and the liquid contained in the flow passage to start in the internal space;
a pump for discharging the mixed solution from the tank; and
a filter that separates one or more components of the mixed solution.

A011
The device according to Embodiment A001,
wherein the liquid is body fluid.

A012
The device according to Embodiment A001 or A011,
wherein the liquid is blood.

A021

The device according to any one of Embodiments A001 to A012, wherein the flow passage includes a capillary tube at least at the one end at which the liquid is received.

A022

The device according to Embodiment A021, wherein the capillary tube comprises a plurality of capillary tubes.

A023

The device according to Embodiment A021 or A022, wherein the or each capillary tube is slit-shaped.

A024

The device according to any one of Embodiments A001 to A023, wherein the flow passage is configured to receive and contain a predetermined amount of the liquid.

A025

The device according to any one of Embodiments A021 to A023, wherein the or each capillary tube of the flow passage has a predetermined length.

A026

The device according to Embodiment A025, wherein a portion of the flow passage that is downstream of the capillary tube (in a direction away from the one end) is configured to impede capillary action.

A031

The device according to any one of Embodiments A001 to A026, wherein the processing solution is sealed in the tank.

A032

The device according to Embodiment A031, wherein the tank includes a tank body and a sealing member that define an inside of the tank.

A033

The device according to Embodiment A032, wherein at least a portion of the sealing member is configured to receive the flow passage member.

A034

The device according to Embodiment A033, wherein the sealing member comprises at least two sealing members, wherein a first one of the sealing members is configured to receive the flow passage member, and wherein a second one of the sealing members is configured to allow the mixed solution to be discharged from the tank.

A035

The device according to any one of Embodiments A032 to A034, wherein the or each sealing member includes a bead and is fixed to an inner wall of the tank body in a mechanically removable manner.

A036

The device according to any one of Embodiments A032 to A035, wherein the or each sealing member includes a breakable film.

A037

The device according to any one of Embodiments A001 to A036, wherein the tank is configured such that the mixed solution is sealed in the tank.

A041

The device according to any one of Embodiments A001 to A037, wherein the processing solution is a diluent.

A051

The device according to any one of Embodiments A001 to A041, wherein the pump includes a syringe.

A052

The device according to any one of Embodiments A001 to A051, wherein the pump includes a pipette valve.

A055

The device according to Embodiment A051 or A052, wherein the pump is configured to apply a pressure to an inside of the flow passage at one of two ends of the flow passage.

A056

The device according to Embodiment A055, wherein to apply the pressure to the inside of the flow passage is to apply a positive pressure or a negative pressure to the inside of the flow passage.

A061

The device according to any one of Embodiments A001 to A056, wherein the tank includes a discharge channel for discharging the mixed solution.

A062

The device according to Embodiment A061, wherein the pump is configured to apply a pressure to the other end of the flow passage to discharge the mixed solution in the flow passage and the tank to an outside through the discharge channel.

A065

The device according to any one of Embodiments A001 to A056, further comprising:

a discharge channel that is in fluid communication with the other end of the flow passage.

A066

The device according to Embodiment A065, wherein the filter is disposed in the discharge channel.

A071

The device according to any one of Embodiments A061 to A065, wherein the discharge channel is in fluid communication with the internal space, and has a second internal space disposed in a path through which the liquid is discharged.

A072

The device according to Embodiment A071, wherein the second internal space is in fluid communication with an outlet of the device, and the mixed solution is discharged through the outlet.

A081

The device according to any one of Embodiments A001 to A072, wherein the filter includes a plasma separation filter or a serum separation filter.

A082

The device according to any one of Embodiments A001 to A081, wherein the filter includes cellulose or glass fibers.

A091

The device according to any one of Embodiments A001 to A082, wherein the filter is configured such that the filter receives the mixed solution and that the mixed solution does not seep from a radially peripheral edge portion of the filter at least at a portion of the filter in a discharge direction in which the mixed solution is discharged.

A092

The device according to any one of Embodiments A061 to A082, wherein the filter is disposed in the discharge channel and is configured such that the filter receives the mixed solution in a region substantially including a center of the filter and that the mixed solution does not seep from a peripheral edge portion of the filter.

A093

The device according to any one of Embodiments A061 to A092, wherein the filter is disposed in the discharge channel, and wherein the discharge channel is configured to guide the mixed solution to a region of the filter that is inside a peripheral portion of the filter.

A095

The device according to any one of Embodiments A091 to A093, wherein the discharge channel includes a portion including a tubular end portion, and wherein the tubular end portion is disposed in close contact with a portion of the filter that is inside the peripheral portion of the filter.

A096

The device according to any one of Embodiments A091 to A093, wherein the filter includes a separation filter, and a guide filter that is disposed upstream of the separation filter in a discharge channel and that is in contact with the separation filter, the guide filter being configured to receive the mixed solution and guide the mixed solution to the separation filter.

A097

The device according to Embodiment A096, wherein the guide filter is disposed in the discharge channel such that the guide filter is not in contact with an inner wall of the discharge channel along a circumferential direction at least at a portion of the guide filter in a discharge direction.

A098

The device according to any one of Embodiments A001 to A082, wherein the guide filter includes, in order along an upstream-to-downstream direction of a discharge channel, a portion that is in contact with an inner wall of the discharge channel and a portion that is not in contact with the inner wall of the discharge channel along a circumferential direction.

A101

The device according to any one of Embodiments A001 to A098, wherein the filter comprises a plurality of filters.

A102

The device according to Embodiment A101, wherein the plurality of filters are stacked in a flow direction of the discharge channel.

A103

The device according to any one of Embodiments A001 to A102, wherein the filter comprises a plurality of filters stacked in a flow-passage direction of the discharge channel.

A104

The device according to any one of Embodiments A101 to A103, wherein the plurality of filters at least include a first filter that is in contact with the inner wall of the discharge channel along the circumferential direction and that is configured to receive substantially all of the mixed solution that flows to the first filter, a second filter disposed in contact with the first filter at a location downstream of the first filter, the second filter being disposed such that the second filter is not in contact with the inner wall of the discharge channel along the circumferential direction at least at a portion of the second filter in the flow direction of the discharge channel, and a third filter disposed in contact with the second filter at a location downstream of the second filter, the third filter having a radius greater than a radius of the second filter and being configured to receive substantially all of the mixed solution discharged from the second filter such that the received mixed solution does not reach a peripheral edge surface of the third filter.

A201

A device that collects liquid, the device comprising:

a flow passage member including a flow passage that receives liquid at one end of the flow passage and that is capable of containing the received liquid;

a tank having an internal space in which a processing solution is contained, the tank being configured to receive at least one end of the flow passage member and allow mixing of the processing solution contained in the tank and the liquid contained in the flow passage to start in the internal space; and a pump for discharging the mixed solution from the tank.

A255

The device according to Embodiment A201, wherein the pump is configured to apply a pressure to an inside of the flow passage at one of two ends of the flow passage.

A261

The device according to Embodiment A201 or A255, wherein the tank includes a discharge channel for discharging the mixed solution.

A262

The device according to Embodiment A261, wherein the pump is configured to apply a pressure to the other end of the flow passage to discharge the mixed solution in the flow passage and the tank to an outside through the discharge channel.

A265

The device according to Embodiment A261, further comprising:

a discharge channel that is in fluid communication with the other end of the flow passage.

A266

The device according to Embodiment A265, wherein the filter is disposed in the discharge channel.

While several embodiments and examples of the present disclosure have been described above, these embodiments and examples have been described to illustrate the present disclosure. For example, each of the above-described embodiments has been described in detail to facilitate understanding of the present disclosure, and additional changes may be made to dimensions, configurations, materials, and circuits as necessary. Embodiments incorporating any combination of one or more of the above-mentioned features of the present disclosure are also included in the scope of the present disclosure. The appended claims are intended to cover various modifications to the embodiments without departing from the spirit of the present disclosure. Accordingly, the embodiments and examples disclosed herein are presented for purposes of illustration and should not be construed as limiting the scope of the present disclosure.

REFERENCE SIGNS LIST 101 target
102, 202 liquid
110, 210 flow passage member
111, 211 flow passage/capillary tube
112, 212 side hole
113, 213 distal end
120, 220 tank
121, 221 internal space
122, 123, 222, 223 sealing member/bead
124 stopper
131, 231 processing solution
132, 232 mixed solution
133, 233 discharged solution
140, 240 discharge channel member
141, 241 first discharge channel member
142, 242 second discharge channel member
143, 243 discharge channel
144, 244 outlet
150, 250 syringe
151, 251 piston
152, 252 cylinder
160, 260 filter
1100, 1200 filter flow passage (device)
1101, 1201 first flow passage member
1102, 1202 second flow passage member
1110, 1210a to 1210c filter
1120, 1220 flow passage
1131, 1231 unfiltered liquid
1132, 1232 filtered liquid
1133, 1233 liquid in filter

The invention claimed is:

1. A device for collecting liquid, the device comprising:
a flow passage member including a flow passage that receives liquid at one end of the flow passage and that is capable of containing received liquid;
a tank having an internal space in which a processing solution is contained, the tank being configured to:
receive at least one end of the flow passage member,
allow the processing solution to contact the liquid while the liquid is being contained in the flow passage, and
form a mixed solution of the processing solution and the liquid in the internal space;
a discharge channel disposed to the tank, for discharging the mixed solution;
a pump, configured to be capable of connecting to the flow passage member and/or the tank, for discharging the mixed solution from the tank; and
a filter disposed to the discharge channel and configured to separate one or more components of the mixed solution.

2. The device according to claim 1, wherein the liquid is blood or saliva.

3. The device according to claim 1, wherein the flow passage includes a capillary tube at least at one end at which the liquid is received.

4. The device according to claim 3, wherein the capillary tube is slit-shaped.

5. The device according to claim 1, wherein the flow passage is configured to receive and contain a predetermined amount of the liquid.

6. The device according to claim 1, wherein the tank includes a tank body and a sealing member that define an inside of the tank, and wherein the processing solution is sealed in the tank.

7. The device according to claim 6, wherein the sealing member includes a bead and is fixed to an inner wall of the tank body in a mechanically removable manner.

8. The device according to claim 6, wherein the sealing member includes a breakable film.

9. The device according to claim 1, wherein the sealing member comprises at least two sealing members, wherein a first one of the sealing members is configured to receive the flow passage member, and wherein a second one of the sealing members is configured to allow the mixed solution to be discharged from the tank.

10. The device according to claim 9, wherein the sealing member includes a bead and is fixed to an inner wall of the tank body in a mechanically removable manner.

11. The device according to claim 9, wherein the sealing member includes a breakable film.

12. The device according to claim 1, wherein the pump is configured to apply a pressure to discharge the mixed solution in the flow passage and the tank to an outside through the discharge channel.

13. The device according to claim 1, wherein the discharge channel is in fluid communication with the flow passage.

14. The device according to claim 1, wherein the filter includes a plasma separation filter or a serum separation filter.

15. The device according to claim 1, wherein the filter is disposed in the discharge channel and is configured such that the filter receives the mixed solution in a region substantially including a center of the filter and that the mixed solution does not seep from a peripheral edge portion of the filter.

16. The device according to claim 1, wherein the discharge channel includes a portion including a tubular end portion, and wherein the tubular end portion is disposed in close contact with a portion of the filter that is inside a peripheral portion of the filter.

17. The device according to claim 1, wherein the filter includes
a separation filter, and
a guide filter that is disposed upstream of the separation filter in a discharge channel and that is in contact with the separation filter, the guide filter being configured to receive the mixed solution and guide the mixed solution to the separation filter, the guide filter being disposed in the discharge channel such that the guide filter is not in contact with an inner wall of the discharge channel along a circumferential direction at least at a portion of the guide filter in a discharge direction.

18. The device according to claim 1, wherein the flow passage member is further configured such that, when one end of the flow passage is received by the tank, the one end of the flow passage is submerged in the processing solution.

19. The device according to claim 1, wherein the pump is further configured to apply pressure to the internal space so as to pass the mixed solution through the discharge channel and the filter.

\* \* \* \* \*